(12) United States Patent
Morone et al.

(10) Patent No.: US 9,951,034 B2
(45) Date of Patent: Apr. 24, 2018

(54) 3-KETOCOUMARINES FOR LED PHOTOCURING

(71) Applicant: LAMBERTI SPA, Albizzate (VA) (IT)

(72) Inventors: Marika Morone, Lipomo (IT); Andrea Bernini Freddi, Gavirate (IT); Gabriele Norcini, Comabbio (IT); Giovanni Floridi, Novara (IT); Giuseppe Li Bassi, Gavirate (IT)

(73) Assignee: IGM RESINS ITALIA S.R.L., Milan (IT)

( * ) Notice: Subject to any disclaimer, the term of this patent is extended or adjusted under 35 U.S.C. 154(b) by 116 days.

(21) Appl. No.: 14/437,779

(22) PCT Filed: Oct. 17, 2013

(86) PCT No.: PCT/EP2013/071784
§ 371 (c)(1),
(2) Date: Apr. 22, 2015

(87) PCT Pub. No.: WO2014/063997
PCT Pub. Date: May 1, 2014

(65) Prior Publication Data
US 2015/0259316 A1  Sep. 17, 2015

(30) Foreign Application Priority Data

Oct. 22, 2012  (IT) ............... VA2012A0041

(51) Int. Cl.
| | | |
|---|---|---|
| *C07D 311/78* | (2006.01) | |
| *C07D 311/16* | (2006.01) | |
| *A61K 6/00* | (2006.01) | |
| *C08F 2/50* | (2006.01) | |

(52) U.S. Cl.
CPC .......... *C07D 311/78* (2013.01); *A61K 6/0052* (2013.01); *C07D 311/16* (2013.01); *C08F 2/50* (2013.01)

(58) Field of Classification Search
CPC .. C07D 311/78; C07D 311/16; A61K 6/0052; C08F 2/50
See application file for complete search history.

(56) References Cited

U.S. PATENT DOCUMENTS

| | | | |
|---|---|---|---|
| 3,844,916 A | | 10/1974 | Gaske |
| 4,147,552 A | * | 4/1979 | Specht ................ C07D 311/16 430/152 |
| 4,278,751 A | | 7/1981 | Specht et al. |
| 4,289,844 A | | 9/1981 | Specht et al. |
| 5,011,755 A | * | 4/1991 | Rohde ....................... C08F 2/50 430/18 |
| 5,482,649 A | | 1/1996 | Meixner et al. |
| 5,734,002 A | | 3/1998 | Reich et al. |
| 2011/0074897 A1 | | 3/2011 | Araki |
| 2012/0029108 A1 | | 2/2012 | Nakane et al. |

FOREIGN PATENT DOCUMENTS

| | | | |
|---|---|---|---|
| EP | 280222 A2 | 8/1988 | |
| EP | 1911814 A1 | 4/2008 | |
| EP | 2388146 A2 | 11/2011 | |
| GB | 1578662 A | 11/1980 | |
| WO | 2006102524 A2 | 9/2006 | |
| WO | WO 2011073404 A1 * | 6/2011 | ........... C09D 11/101 |
| WO | 2012062692 A1 | 5/2012 | |

OTHER PUBLICATIONS

Rao et al. "Condensation of a-Aroylketene Dithioacetals and 2-Hydroxyarylaldehydes Results in Facile Synthesis of a Combinatorial Library of 3-Aroylcoumarins", J. Org. Chem. 2006, 71, 8715-8723.*

* cited by examiner

*Primary Examiner* — Nicole Buie-Hatcher
(74) *Attorney, Agent, or Firm* — Mossman, Kumar & Tyler, PC

(57) ABSTRACT

The present invention relates to 3-ketocoumarines which can be used as photoinitiators in LED photocuring and to a process for curing compositions comprising said 3-ketocoumarines.

15 Claims, No Drawings

3-KETOCOUMARINES FOR LED PHOTOCURING

TECHNICAL FIELD

The present invention relates to 3-ketocoumarines which can be used as photoinitiators in LED photocuring and to a process for photocuring compositions comprising said 3-ketocoumarines.

PRIOR ART

Photopolymerizable systems contain photoinitiators that possess in the molecule a functional group which, by exposure to light radiation of appropriate wavelength, generate radicals able to initiate the polymerization.

Among the light radiation sources used in this field, light emitting diodes (LED), a semiconductor light source, have been the subject of significant development over the past few years because of the advantages of low temperature operation and extremely long life in comparison with conventional medium pressure mercury arc curing lamps. LED lamps are advantageous because of the inherently small size of LED units, their longer lifetime, their robustness and their ability to be easily engineered, for example into commercial printing systems.

When using LED lamps to photocure inks and coatings, it is necessary to use selected photoinitiator systems that are tuned to the wavelength of this light source. While Mercury arc lamps typically have a polychromatic emission spectrum, emitting light in all regions of the UV-visible spectrum from 200 to 450 nm, LED lamps usually have only a single emission band in the range 365-420 nm.

Photoinitiators, absorbing in the region between 365 nm and 420 nm and, are thus required to make full use of the recent development of LEDs with increasing power. Moreover, since high concentration of photoactive substance are usually required for LED applications, the photoinitiators should have a high compatibility with the photopolymerizable system. Thioxanthones, such as isopropyl thioxanthone (ITX) and its derivatives, and acyl phosphine oxides are photoinitiators commonly used in this field.

Unfortunately, the thioxanthone derivatives commonly used both as photoinitiators and sensitizers are prone to yellowing upon exposure, thereby forming degradation products with limited stability. As a result, the original yellowing can shift unpredictably upon storage. Especially in imaging, e.g. inkjet printing, this unstable yellowing behavior makes quite difficult the control of the image tone in the final image.

Acyl phosphine oxides initiators, on the other hand, result in medium volatile aldehyde type of degradation products, producing a background smell of the cured coatings or the printed image, which is no more acceptable. Moreover, the use of high amounts of acyl phosphine oxides initiators creates several health and safety problems.

Alpha-diketones, such as camphorquinone and its derivatives and 1-phenyl propandione, are examples of different photoinitiators which have been used in combination with LED light sources, particularly for dental applications, but unfortunately their activity is quite low, in particular in pigmented system.

Therefore, there is an increasing demand for the development of different photoinitiators, absorbing in the region between 365 nm and 420 nm, having a predictable yellowing behavior, good photochemical reactivity, no odorous degradation products and no health or safety drawbacks.

Coumarine derivatives have been proposed for a long time as photoinitiators and, in particular, as sensitizers working at wavelengths up to about 550 nm, but always using broad spectrum actinic lamps.

GB 1,578,662 describe a composition comprising an unsaturated radiation sensitive material or a photopolymerizable azide material which material contains, as sensitizer, a 3-substituted coumarin compound, which can be also a 3-ketocoumarine. U.S. Pat. No. 4,278,751 discloses a photopolymerizable composition containing at least a polymerizable compound containing ethylenic unsaturations, a photopolymerization activator (photoinitiator) and an amine substituted ketocoumarine sensitizer. Light sources which may be used include broad spectrum light sources, filtered or unfiltered, including Xenon or carbon arcs, narrow spectrum sources such as mercury lamps.

U.S. Pat. No. 4,289,844 discloses a photopolymerizable composition containing at least a polymerizable compound having an polymerizable compound containing ethylenic unsaturation, a photopolymerization activator (photoinitiator) and a sensitizer, selected among 3-ketocoumarines containing $C_1$-$C_{12}$ alkyl or alkenyl group or carbocyclic or heterocyclic group having 5-20 carbon and hetero atoms. In this patent a medium pressure mercury lamp is used as light source.

Surprisingly, we have found that specific derivatives of aromatic 3-ketocoumarines show a high cure speed on exposure to LED light source with wavelength comprised between 365 and 420 nm compared with state of the art photoinitiators and other 3-ketocoumarines. They do not show undesired yellowing behavior and maintain at the same time superior compatibility with photopolymerizable systems.

Therefore the object of the present invention are specific aromatic derivatives of 3-ketocoumarine and a process for photocuring photopolymerizable compositions including these aromatic derivatives both as photoinitiators and as sensitizers. Such photopolymerizable compositions have been found to be suitable for inclusion in ink or coating compositions which are curable on exposure to radiation from a LED light source.

In the present text, with sensitizer we mean a compound that, through a process of energy transfer, activates the photoinitiator at wavelength where the photoinitiator alone would not be reactive.

DESCRIPTION OF THE INVENTION

It is an object of the present invention a process for photocuring photopolymerizable compositions, which process comprises:
I) preparing a photopolymerizable composition comprising:
a) from 50 to 99.9% by weight, preferably from 70 to 98.9% by weight, of at least one ethylenically unsaturated compound;
b) from 0.1 to 35% by weight, preferably from 0.1 to 20% by weight, and more preferably from 0.2 to 15% by weight of at least one 3-ketocoumarine of formula I:

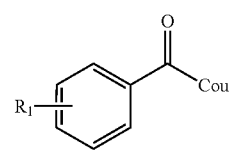

I wherein:

$R_1$ is hydrogen or a substituted or unsubstituted $C_1$-$C_{12}$ alkyl group;

Cou is a coumarine group of formula:

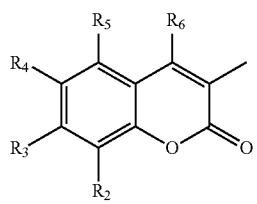

(a)

wherein:

$R_2$, $R_3$, $R_4$ and $R_5$ are, independently of one another, hydrogen; or —S—$R_7$, where $R_7$ is hydrogen, $C_1$-$C_{12}$ alkyl, $C_3$-$C_{12}$ alkenyl, substituted or unsubstituted phenyl, aryl or heteroaryl, $C_5$-$C_6$ cycloalkyl, $C_1$-$C_{12}$ alkyl which is substituted with SH, —N($C_1$-$C_6$ alkyl)$_2$, piperidino, morpholino, piperazino, —OH, —O($C_1$-$C_{12}$ alkyl), —COOH; or $C_1$-$C_{12}$ alkoxy; and at least one of $R_2$, $R_3$, $R_4$ and $R_5$ is different from H;

$R_6$ is hydrogen, a hydroxyl group or an alkyl group having from 1 to 4 carbon atoms;

or Cou is a substituted or unsubstituted naphtho-coumarine group of formula:

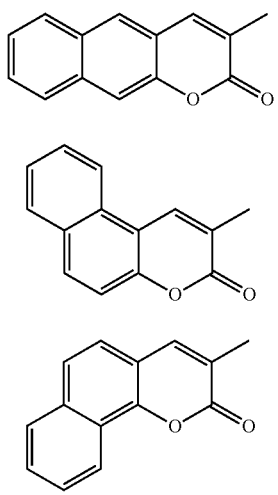

provided that at least one of $R_2$, $R_3$, $R_4$ and $R_5$ is different from H and that, when Cou is (a) and at least one of $R_2$, $R_3$, $R_4$ and $R_5$ is $C_1$-$C_{12}$ alkoxy or when Cou is (b), (c) or (d), $R_1$ is a substituted or unsubstituted $C_1$-$C_{12}$ alkyl group;

II) photopolimerizing the photopolymerizable composition so obtained with a LED light source emitting at wavelengths comprised between 365 nm and 420 nm.

It is a further object of the present invention 3-ketocoumarines of formula I:

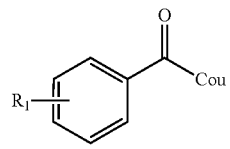

I wherein:

$R_1$ is a substituted or unsubstituted $C_2$-$C_{12}$ alkyl group;

Cou is a coumarine group of formula:

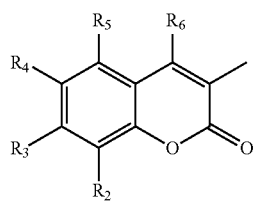

(a)

wherein at least one of $R_2$, $R_3$, $R_4$ and $R_5$ is an alkoxy group having from 1 to 6 carbon atoms and $R_6$ is hydrogen, a hydroxyl group or an alkyl group having from 1 to 4 carbon atoms;

or Cou is a substituted or unsubstituted naphtho-coumarine of formula:

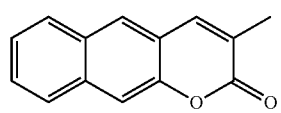

It is a another object of the present invention 3-ketocoumarines of formula I:

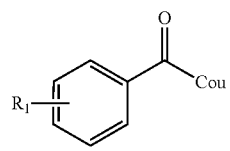

I wherein:

$R_1$ is hydrogen or a substituted or unsubstituted $C_1$-$C_{12}$ alkyl group;

Cou is a coumarine group of formula:

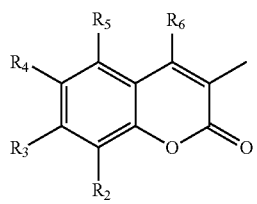

wherein at least one of $R_2$, $R_3$, $R_4$ and $R_5$ is —S—$R_7$, wherein $R_7$ is hydrogen, $C_1$-$C_{12}$ alkyl, $C_3$-$C_{12}$ alkenyl, substituted or unsubstituted phenyl, aryl or heteroaryl, $C_5$-$C_6$ cycloalkyl, $C_1$-$C_{12}$ alkyl which is substituted with SH, —N($C_1$-$C_6$ alkyl)$_2$, piperidino, morpholino, piperazino, —OH, —O($C_1$-$C_{12}$ alkyl), —COOH, and $R_6$ is hydrogen, a hydroxyl group or an alkyl group having from 1 to 4 carbon atoms.

DETAILED DESCRIPTION OF THE INVENTION

In the present text the expressions "alkyl" or "alkyl group" mean, where not differently indicated, a linear or branched alkyl chain containing from 1 to 12 carbon atoms and includes all possible variants for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethylpropyl, 2,2-dimethylpropyl and 2-methyl-butyl etc.

The expressions "cycloalkyl" or "cycloalkyl group" mean, where not differently indicated, a aliphatic ring containing from 4 to 12 carbon atoms which can be, for example, cyclopentyl, cyclohexyl, cyclooctyl, cyclododecyl and the like.

The expressions "aryl" or "aryl group" mean for example substituted or unsubstituted phenyl group, substituted or unsubstituted naphthyl group, anthracenyl group, indenyl group, fluorenyl group and others.

The expressions "heteroaryl" or "heteroaryl group" mean for example furan, thiophene, pyrrole, oxazole, isooxazole, thiazole, isothiazole, imidazole, pyrazole, pyrane, pyridine, pyrrolidine, piperidine, indole, quinoline, isoquinoline, xanthene, carbazole, acridine, indeline, julolidine and others.

"Alkenyl" or "alkenyl group" mean an unsaturated group containing from 3 to 12 carbon atom which can be, for example, allyl, methallyl or undecenyl.

The term substituted means that a group bears a substituent that can be halogen atom, an alkyl, cycloalkyl, alkoxy, alkylamino, dialkylamino, alkylthio or arylthio group, heterocyclic groups, more specifically, methyl, ethyl, isopropyl, tert-butyl, phenyl, trifluoromethyl, cyano, acetyl, ethoxycarbonyl, carboxyl, carboxylate, amino, methylamino, dimethylamino, ethylamino, diethylamino, isopropylamino, diisopropylamino, cyclohexylamino, dicyclohexylamino, acetylamino, piperidino, pyrrolidyl, methoxy, ethoxy, propoxy, isopropoxy, butoxy, pentyloxy, phenoxy, hydroxyl, acetoxy, —PO$_3$H, methylthio, ethylthio, i-propylthio, n-propylthio, phenyltio, mercapto, acetylthio, thiocyano, methylsulfinyl, methylsulthnyl, dimethylsulfonyl, sulfonate groups, fluorine atom, chlorine atom, bromine atom, iodine atom, trimethylsilyl, triethylsilyl, trimethylstannyl, furyl, thienyl, pyridyl, piperidino, morpholino, pyrrolidyl groups and so on.

Among the substituents mentioned in the preceding paragraph, electron donating groups such as alkoxy groups, for example methoxy, ethoxy, isopropoxy, tert-butoxy or phenoxy groups; methyl, ethyl, isopropyl, hydroxyl, acetoxy, benzoyloxy groups, etc. or a thioalkyl group, such as methylthio, ethylthio, n-propylthio, i-propylthio, butylthio, pentylthio, or a arylthio group, such as phenylthio, are preferably contained.

$R_1$ in formula I is preferably a substituted or unsubstituted $C_2$-$C_{12}$ alkyl group, more preferably a $C_2$-$C_6$, alkyl group having from 2 to 6 carbon atoms.

3-ketocoumarines of formula I, wherein Cou is a coumarine group of formula (a) in which at least one of $R_2$, $R_3$, $R_4$ and $R_5$ is a $C_1$-$C_6$, in particular a $C_1$-$C_3$ alkoxy group, or is —S—$R_7$, wherein $R_7$ is an alkyl group having from 1 to 6, in particular from 1 to 3, carbon atoms, are preferred for the realization of the present invention.

$R_6$ is preferably hydrogen.

In another preferred embodiment of the present invention, Cou is a unsubstituted naphtho-coumarine group of formula (b), (c) or (d).

In another preferred embodiment, in the 3-ketocoumarine of formula I, Cou is a coumarine group of formula (a) in which $R_6$ is hydrogen, at least two of $R_2$, $R_3$, $R_4$ and $R_5$ are a $C_1$-$C_6$ alkoxy group and $R_1$ is a substituted or unsubstituted $C_1$-$C_{12}$ alkyl group.

The compounds represented by formula I can be prepared according conventional methods known to the expert in the art. For example, they can be synthesized by a Knoevenagel condensation of 2-hydroxy-1-arylaldehyde(-arylketone) with the corresponding alkyl benzoylacetate, as schematized below:

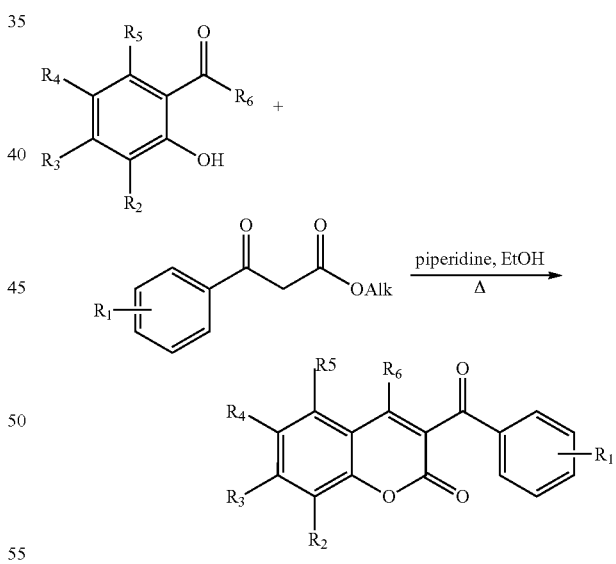

where $R_1$, $R_2$, $R_3$, $R_4$, $R_5$ and $R_6$ have the same meaning as reported above.

The photopolymerizable compositions of the invention can also conveniently include a co-initiator, which is a molecule that acts as hydrogen donor that increases the polymerization rate. The co-initiators are known in the art and they are typically alcohols, thiols, amines or ethers that have an available hydrogen, bonded to a carbon adjacent to the heteroatom. Such co-initiators are generally present in an amount comprised between 0.2 and 15% by weight, preferably from 0.2 to 8% by weight. Suitable co-initiators include, but are not limited to, aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, ciclohexyl amine, benzyldimethyl amine, di-cyclohexyl amine, N-phenyl glycine, triethyl amine, phenyldiethanol amine, triethanolamine, piperidine, piperazine, morpholine, pyridine, quinoline, esters of dimethylamino benzoic acid, Michler's ketone (4,4'-bis-dimethyl aminobenzophenone) and corresponding derivatives.

As the amine co-initiator, an amine-modified acrylate compound can be used, examples of such amine-modified acrylate include acrylates modified by reaction with a primary or secondary amine that are described in U.S. Pat. No. 3,844,916, EP 280222, U.S. Pat. Nos. 5,482,649 or 5,734, 002.

Preferred co-initiators are Esacure A198 (bis-N,N-[4-dimethylaminobenzoyl) oxyethylen-1-yl]-methylamine) and Esacure EDB (ethyl-4-dimethylamino benzoate) both commercialized by Lamberti S.p.A., IT, 2-ethylhexyl-4-dimethylaminobenzoate and N-phenyl glycine.

The photopolymerizable compositions of the invention can also conveniently include other photoinitiators commonly used in the field.

Examples of photoinitiators which can be used in combination with the 3-ketocoumarines of formula I include acylphosphine oxides, both monoacylphosphine oxides and bisacylphosphine oxides, coumarines or other ketocoumarines, aromatic onium salt compounds, organic peroxides, thioxanthones, hexaaryl bisimidazoles, ketoxime esters, borate compounds, azinium compounds, metallocene compounds, benzophenones, α-diketones, ketosulfones, α-aminoketones, benzoin and benzoin ethers, benzil ketals, α-hydroxyketones and mixture thereof.

Examples of thioxanthone derivatives are thioxanthone, diethylthioxanthone, 2-isopropylthioxanthone, 2-chlorothioxanthone, 2,4-diethylthioxanthone or those described in the patent application PCT/EP2011/069514, such as n-dodecyl-7-methyl-thioxanthone-3-carboxylate and N,N-disobutyl-7-methyl-thioxanthone-3-carbamide.

Examples of α-hydroxyketones and α-aminoketones are 1-hydroxy cyclohexylphenyl ketone, 2-hydroxy-2-methyl-1-phenyl-propane-1-one, 1-[4-(2-hydroxyethoxy)phenyl]-2-hydroxy-2-methyl-1-propane-1-one, 2-hydroxy-1-{4-[4-(2-hydroxy-2-methyl-propionyl)-benzyl]phenyl}-2-methyl-propane-1-one), 2-methyl-1-(4-methylthiophenyl)-2-morpholinopropane-1-one), 2-benzyl-2-dimethylamino-1-(4-morpholinophenyl)-butanone-1, and (2-(dimethylamino)-2-[(4-methylphenyl)methyl]-1-[4-(4-morpholinyl)phenyl]-1-butanone).

Examples of oxime-based photoinitiators are 1,2-octanedione,1-[4-(phenylthio)phenyl]-,2-(O-benzoyloxime) and ethanone, 1-[9-ethyl-6-(2-methylbenzoyl)-9H-carbazole-3-yl], 1-(O-acetyloxime).

Examples of the acylphosphine-based photoinitiators include, but are not limited to, bis(2,4,6-trimethylbenzoyl) phenylphosphine oxide, 2,4,6-trimethylbenzoyl-diphenyl phosphine oxide and bis(2,6-dimethoxybenzoyl)-2,4,4-trimethylpentyl phosphine oxide.

Examples of coumarine derivatives may include 4-methyl-7-dimethylamino coumarine, 4-methyl-7-ethylamino coumarine, 4-methylpiperidino[3.2-g]coumarine, 4-methyl-7-cyclohexyl amino coumarine, 4-trifluoromethyl-7-diethylamino coumarine, 3-phenyl-4-methyl-7-diethylamino coumarine, 3-(2'-N-methyl benzimidazoyl)-7-diethylamino coumarine, 4-trifluoromethyl-6-methyl-7-ethylamino coumarine and 3-phenyl-7-amino coumarine.

Other specific examples of photoinitiators include acetophenone, acetophenone benzil ketal, 2,2-dimethoxy-2-phenylacetophenone, xanthone, fluorenone, anthraquinone, 3-methylacetophenone, 4-chlorobenzophenone, 4,4'-dimethoxybenzophenone, 4,4'-diaminobenzo phenone, Michler's ketone, benzoin propyl ether, benzoin ethyl ether and benzil dimethyl ketal.

Preferred additional photoinitiators are acylphosphine oxides, α-hydroxyketones, α-aminoketones, ketosulfones, alpha-diketones and bi-functional photoinitiators, for example Esacure 1001 and Esacure ONE (both commercialized by Lamberti S.p.A., IT).

The additional photoinitiators or mixture of different photoinitiators can be added to the photopolymerizable compositions of the invention in an amount comprised between 0.5 and 15% by weight, preferably between 1 and 8% by weight.

In a particularly preferred embodiment of the invention the 3-ketocoumarine of formula I are used as sensitizers of sensitizable photoinitiators in photopolymerizable compositions.

In this case, the photopolymerizable composition comprises from 70 to 98.9% by weight of at least one photopolymerizable compound, from 0.1 to 10% by weight of at least one 3-ketocoumarine of formula I, as sensitizer and from 1 to a 15% by weight at least one sensitizable photoinitiator, for example a ketosulfone or an α-aminoketone and, optionally, from 0.2 to 8% by weight of a co-initiator.

The preferred sensitizable photoinitiator are 1-[4-[(4-benzoyl-phenyl)-thio]-phenyl]-2-methyl,2-[(4-methyl-phenyl)-sulfonyl]-propan-1-one (Esacure 1001, from Lamberti S.p.A.), 2-methyl-1-(4-methylthiophenyl)-2-morpholinopropane-1-one), 2-benzyl-2-dimethylamino-1-(4-morpholinophenyl)-butanone-1, and (2-(dimethylamino)-2-[(4-methylphenyl)methyl]-1-[4-(4-morpholinyl)phenyl]-1-butanone).

By ethylenically unsaturated compound we mean a monomer, oligomer, prepolymer having at least one unsaturated double bond, or a mixture thereof, capable of undergoing radical polymerization. Also monomer combinations, oligomers and prepolymers with different degrees of unsaturation can be used.

The monomers suitable for the realization of the present invention are those commonly used in the field and can be chosen, for example, among vinyl ethers, N-vinyl pyrrolidone, N-vinyl caprolactam, mono- and poly-functional allyl ethers such as trimethylol propane diallyl ether, styrenes and alpha-methyl styrenes, esters of (meth)acrylic acid with aliphatic alcohol, glycols, polyhydroxylated compounds such as pentaerythritol or trimethylol propane, esters of vinyl alcohol with acrylic or aliphatic acid, derivatives of fumaric and maleic acids.

Suitable oligomers or prepolymers for the present invention comprise, for example, polyesters, polyacrylates, polyurethanes, epoxy resins, polyethers with acrylic, maleic or fumaric functionalities.

Monomers, oligomers and prepolymers, which are commonly used in photopolymerizable ink are preferred. These compounds are well known to the expert in the art and are described for example in EP 1911814, US 2012/029108, US 2011/0074897, WO 2006/102524 and EP 2388146 Specific examples include monofunctional, difunctional and polyfunctional monomers such as the compounds represented by the formulae reported below:

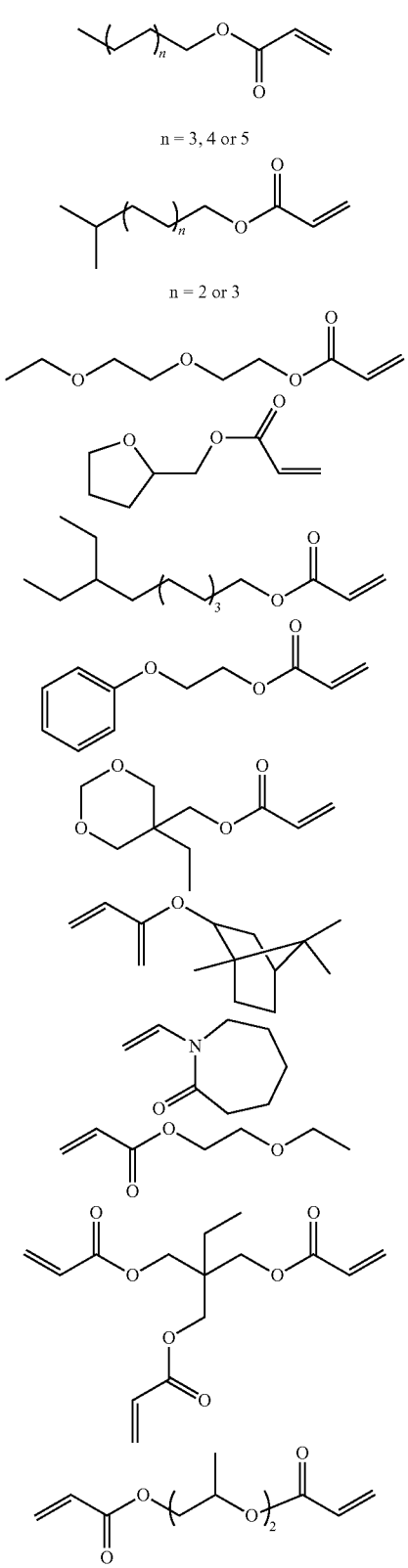

Besides the above-mentioned compounds, other components normally used in the field and known to the experts in the art can be added to the photopolymerizable compositions of the invention. For example, thermal stabilizers, photo-oxidation stabilizers, anti-oxidants, fillers, dispersants, coloring and/or opacifying substances and other additives of general use. Others components of the photopolymerizable compositions of the invention can be non-photopolymerizable polymers present as chemically inert substances, as an example nitrocellulose, polyacrylic esters, polyolefins etc.

The process claimed in the present invention is useful in the coating of metallic, wood, paper and plastic surfaces.

The 3-ketocoumarines of formula I work both in transparent photopolymerizable compositions and in non-transparent or colored compositions and, in particular, are useful for the preparation of inks photopolymerizable with a LED light source. These photoinitiators are particularly suited for the preparation of photopolymerizable inks for ink-jet printing.

For this reason the photopolymerizable composition of the invention can further comprise from 0.01 to 30% by weight of colorants.

Colorants which can be used in the LED photopolymerizable inks of the invention are dyes, pigments or a combination thereof. Organic and/or inorganic pigments may be used. The colorants are preferably pigments or polymeric dyes, most preferably pigments. The pigments may be black, white, cyan, magenta, yellow, red, orange, violet, blue, green, brown, mixtures thereof, and the like.

Exemplary organic pigments include insoluble azo pigments, condensed azo pigments, azo lake, and chelate azo pigments; polycyclic pigments, such as phthalocyanine pigments, perylene and perinone pigments, anthraquinone pigments, quinacridone pigments, dioxane pigments, thioindigo pigments, isoindolinone pigments, and quinophthalone pigments; dye chelates, such as basic dye chelates and acid dye chelates; dye lakes, such as basic dye lakes and acid dye lakes; and nitro pigments, nitroso pigments, aniline black, and fluorescent pigments.

For LED photopolymerizable white inks, the white colorants are preferably present in an amount of 3% to 30% by weight of the ink composition, and more preferably 5% to 25%. Usually the other colorants are present in the LED photopolymerizable inks of the invention in the range of 0.01 to 10% by weight, preferably in the range of 0.1 to 5% by weight. Colorants for ink-jet printing are particularly preferred.

In addition to the main components, the LED photopolymerizable inks can contain also other specific ingredients such as co-initiators and other photoinitiators, such as those described in the preceding paragraphs and in the same amount, dispersants, surfactants and other additives which are well known to the expert in the art. The choice of these components is not particularly limited.

The dispersants are added to the inks so as to enhance the dispersibility of the pigment. For the realization of the present invention, a dispersant that is generally used for preparing a pigment-dispersed liquid, such as a polymeric dispersant, can be used. Examples of such polymeric dispersant include polyoxyalkylene, polyalkylene polyamines, vinyl polymers and copolymers, acrylic polymers and copolymers, polyesters, polyamides, polyimides, polyurethanes, amino polymers, silicon-containing polymers, sulfur-containing polymers, fluorine-containing polymers, and epoxy resins.

Examples of preparation of 3-ketocoumarines of formula I and photopolymerizable compositions according to the invention, only for illustrative purpose and not limitative, are reported in the following paragraphs.

EXAMPLES

Example 1 (Comparative)

Preparation of 3-benzoyl-7-(N,N-diethylamino)coumarin

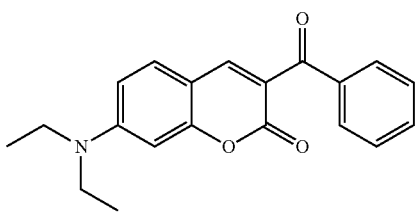 [SMILES: CCN(CC)c1ccc2cc(C(=O)c3ccccc3)c(=O)oc2c1]

0.49 g (2.58 mmoles) of ethyl benzoylacetate and 0.3 g (3.52 mmoles) of piperidine were added under stirring to a solution of 0.5 g (2.58 mmoles) of 4-(N,N-diethylamino)-2-hydroxy-benzaldehyde in 10 ml of ethanol. After 2 hours under reflux the reaction mass was cooled down.

After crystallization at room temperature, the reaction product was filtered and dried, obtaining 0.6 g (1.86 mmoles, yield 72%) of yellow crystals.

m.p. 147-150° C.

$^1$H-NMR (CDCl$_3$, δ ppm): 1.24 (t, 6H), 3.45 (q, 4H), 6.50 (d, 1H), 6.62 (dd, 1H), 7.35 (d, 1H), 7.45 (m, 2H), 7.55 (m, 1H), 7.81 (d, 2H), 8.09 (s, 1H).

Example 2 (Comparative)

Preparation of 2,3,5,6-1H,4H-tetrahydroquinolizino[9,9a,1-gh]coumarin, 9-benzoyl

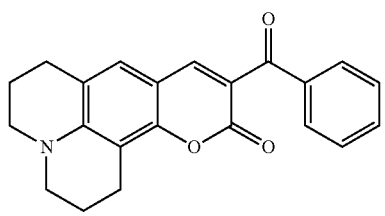 [SMILES: O=C(c1ccccc1)c1cc2cc3c4c(c2oc1=O)CCCN4CCC3]

0.21 g (1.10 mmoles) of ethyl benzoylacetate and 0.21 g (1.10 mmoles) of piperidine were added under stirring to a solution of 0.3 g (1.10 mmoles) of 2,3,6,7-tetrahydro-8-hydroxy-1H,5H-benzo[ij]quinolizine-9-carboxaldehyde in 10 ml of ethanol. After two hours under reflux, the reaction mass was cooled to room temperature and the solvent was removed by distillation under vacuum. The reaction product was purified by flash chromatography on silica gel (methylene chloride) obtaining 0.3 g (0.68 mmoles, yield 78%) of orange-red crystals.

m.p. 194-196° C.

$^1$H-NMR (CDCl$_3$, δ ppm): 2.00 (m, 4H), 2.28 (t, 2H), 2.94 (t, 2H), 3.35 (m, 4H), 6.95 (s, 1H), 7.45 (t, 2H), 7.55 (m, 1H), 7.81 (d, 2H), 8.03 (s, 1H).

Example 3 (Comparative)

Preparation of 3-benzoyl-7-methoxycoumarin

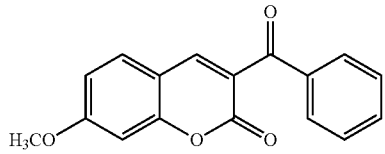 [SMILES: COc1ccc2cc(C(=O)c3ccccc3)c(=O)oc2c1]

0.37 g (1.90 mmoles) of ethyl benzoylacetate and 0.16 g (1.90 mmoles) of piperydine were added under stirring to a solution of 0.3 g (1.90 mmoles) of 4-methoxy-2-hydroxy-benzaldehyde in 7 ml of ethanol. After two hours at reflux the reaction mass was cooled to room temperature and the solvent was removed by distillation under vacuum. The reaction product was purified by flash chromatography on silica gel (methylene chloride:ethyl acetate 95:5) obtaining 0.42 g (1.49 mmoles, yield 78%) of light-yellow crystals.

m.p. 150-153° C.; $^1$H-NMR (CDCl$_3$, δ ppm): 3.91 (s, 3H), 6.90 (m, 2H), 7.42-7.51 (m, 3H), 7.60 (m, 1H), 7.86 (d, 2H), 8.10 (s, 1H).

Example 4

Preparation of 7-methoxy-3-(4-tertbutyl-benzoyl)coumarin

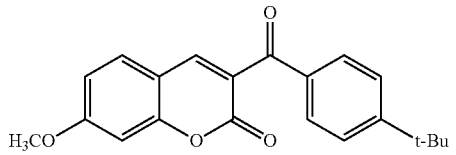 [SMILES: COc1ccc2cc(C(=O)c3ccc(C(C)(C)C)cc3)c(=O)oc2c1]

Preparation of methyl 3-(4-t-butylphenyl)-3-oxo-propanoate 15.6 g (0.129 mmoles) of 33% NaOH were added dropwise to a solution of 15 g (0.129 mmoles) of methyl acetoacetate in 50% THF/water solution at 0° C. under stirring.

After 90 min, 25.5 g (0.130 mmoles) of 4-t-butyl-benzoyl chloride were added and the mixture was heated to 60° C. under stirring for 60'. After cooling at room temperature the reaction mass was diluted with 200 ml of water and 200 ml of methylene chloride. The organic phase was separated and anhydrified with sodium sulphate. The solvent was removed by distillation under vacuum obtaining the crude methyl 3-(4-t-butylphenyl)-3-oxo-propanoate as a yellow oil.

Preparation of 7-methoxy-3-(4-tertbutylbenzoyl)coumarin 0.76 g (3.28 mmoles) of the methyl 3-(4-t-butylphenyl)-3-oxo-propanoate were added to a solution of 0.5 g (3.28 mmoles) of 4-methoxy-2-hydroxy-benzaldehyde and 0.28 g (3.28 mmoles) of piperidine in 10 ml of ethanol. The solution was stirred under reflux for 2 hrs. After cooling at room temperature the solvent was removed by distillation under vacuum. The reaction product was purified by flash chromatography on silica gel (methylene chloride:ethyl acetate 95:5) obtaining 0.50 g (1.48 mmoles, yield 50%) of light-yellow crystals.

m.p. 123-127° C.

$^1$H-NMR (CDCl$_3$, δ ppm): 1.30 (s, 9H), 3.86 (s, 3H), 6.75-6.90 (m, 2H), 7.40-7.50 (m, 3H), 7.76 (d, 2H), 8.00 (s, 1H).

Example 5

Preparation of 3-(4-tertbutylbenzoyl)benzo[f]coumarin

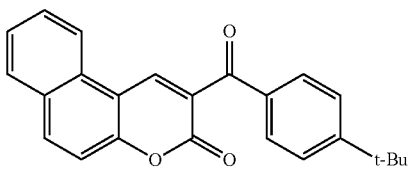 [SMILES: CC(C)(C)c1ccc(C(=O)c2cc3c(ccc4ccccc43)oc2=O)cc1]

Preparation of 2-hydroxy-naphthalene 1-carbaldehyde 66 g of NaOH 33% water solution (520 mmoles) were added to a solution of 15 g (104 mmoles) of 2-hydroxynaphthalene in 200 ml of methanol. After 30 min under stirring, 20 g (165 mmoles) of trichloromethane were slowly added maintaining the temperature at 60° C. After 2 hrs the reaction mixture was cooled to room temperature and the solvent removed by distillation under vacuum. The reaction product was dissolved in 200 ml of methylene chloride and washed with 100 ml of 5% hydrochloric acid. The organic phase was separated and after evaporation under vacuum of the solvent, the 2-hydroxy-naphthalene 1-carbaldehyde was purified by flash chromatography on silica gel (toluene) obtaining 8.7 g (yield 48%) of white crystals.

$^1$H-NMR (CDCl$_3$, δ ppm): 7.25 (d, 1H), 7.45 (t, 1H), 7.63 (t, 1H), 7.80 (d, 1H), 8.00 (d, 1H), 8.38 (d, 1H), 10.84 (s, 1H).

Preparation of 3-(4-tertbutylbenzoyl)benzo[f]coumarin 1.6 g (6.83 mmoles) of crude methyl 3-(4-t-butylphenyl)-3-oxo-propanoate, prepared as reported in the Example 4, and 0.4 g (4.64 mmoles) of piperidine were added under stirring to a solution of 0.8 g (4.64 mmoles) of 2-hydroxy-naphthalene 1-carbaldehyde in 10 ml of ethanol. After two hours under reflux, the reaction mixture was cooled down. The reaction product, crystallized at room temperature, was recovered by filtration. 0.76 g (yield 47%) of product were obtained.

m.p. 161-163° C.

$^1$H-NMR (CDCl$_3$, δ ppm): 1.35 (s, 9H), 7.48-7.56 (m, 3H), 7.58-7.65 (t, 1H), 7.68-7.75 (t, 1H), 7.85-7.90 (m, 2H), 7.92-7.70 (d, 1H), 8.08-8.12 (d, 1H), 8.23-8.28 (d, 1H), 8.87 (s, 1H).

Example 6

Preparation of 7-ethylthio-3-benzoylcoumarin

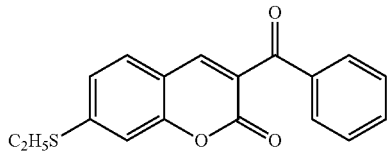

Preparation of 4-ethylthio-2-hydroxy-benzaldehyde 3 g (19 mmoles) of 3-ethylthio-phenol were added under stirring in nitrogen atmosphere to a solution of 1.76 g (58.2 mmoles) of anhydrous paraformaldehyde, 5.31 (52.5 mmoles) of anhydrous triethylamine and 5 g (52.5 mmoles) of anhydrous MgCl$_2$ in 100 ml of anhydrous THF. After 40 min at 60° C. the reaction mixture was cooled at room temperature, diluted with 100 ml of water and acidified to pH 1 with hydrochloric acid. After extraction with ethylacetate and evaporation under vacuum of the solvent, the crude product was purified by flash chromatography on silica gel (methylene chloride) obtaining 2.0 g (yield 57%) of 4-ethylthio-2-hydroxy-benzaldehyde as yellow oil.

$^1$H-NMR (CDCl$_3$, δ ppm): 1.40 (t, 3H), 3.05 (q, 2H), 6.58 (s, 1H), 6.59 (d, 1H), 7.40 (d, 1H), 9.80 (s, 1H).

Preparation of 7-ethylthio-3-benzoyl coumarin 0.83 g (4.33 mmoles) of ethyl benzoylacetate and 0.37 g (4.33 mmoles) of piperidine were added to a solution of 0.79 g (4.33 mmoles) of 4-ethylthio-2-hydroxy-benzaldehyde in 10 ml of ethanol. The mixture was stirred for two hours under reflux, then cooled down. After crystallization at room temperature, the reaction product was collected by filtration obtaining 0.90 g of light yellow crystals (yield 67%).

m.p. 122-124° C.

$^1$H-NMR (CDCl$_3$, δ ppm): 1.45 (t, 3H), 3.08 (q, 2H), 7.18 (d, 2H), 7.42-7.55 (m, 3H), 7.60-7.65 (m, 1H), 7.88 (d. 1H), 8.08 (s, 1H).

Example 7 (Comparative)

Preparation of 3-benzoyl-5,7-dimethoxycoumarin

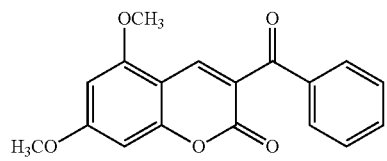 [SMILES: COc1cc(OC)c2cc(C(=O)c3ccccc3)c(=O)oc2c1]

Preparation of 4,6-dimethoxy-2-hydroxy-benzaldehyde 3 g (19.5 mmoles) of 3,5-dimethoxy-phenol were added under stirring in nitrogen atmosphere to a solution of 1.76 g (58.2 mmoles) of anhydrous paraformaldehyde, 5.31 g (52.5 mmoles) of anhydrous triethylamine and 5 g (52.5 mmoles) of anhydrous MgCl$_2$ in 100 ml of anhydrous THF. After 40 min at 60° C. the reaction mixture was cooled at room temperature, diluted with 100 ml of water and acidified to pH 1 with hydrochloric acid. After extraction with ethyl acetate and evaporation of the solvent under vacuum, the crude product was purified by flash chromatography on silica gel (methylene chloride) obtaining 0.6 g (yield 17%) of 4,6-dimethoxy-2-hydroxy-benzaldehyde as white solid.

$^1$H-NMR (CDCl$_3$, δ ppm): 3.84 (s, 3H), 3.85 (s, 3H), 5.91 (s, 1H), 6.02 (s, 1H), 10.10 (s, 1H).

Preparation of 3-benzoyl-5,7-dimethoxycoumarin 0.63 g (3.29 mmoles) of ethyl benzoylacetate and 0.28 g (3.29 mmoles) of piperidine were added to a solution of 0.60 g (3.29 mmoles) of 4,6-dimethoxy-2-hydroxy-benzaldehyde in 10 ml of ethanol. The mixture was stirred for two hours under reflux, then cooled down. After crystallization at room temperature, the reaction product was recovered by filtration obtaining 0.80 g of white crystals (yield 78%).

m.p. 175-178° C.

$^1$H-NMR (CDCl$_3$, δ ppm): 3.92 (s, 6H), 6.30 (s, 1H), 6.47 (s, 1H), 7.45 (t, 2H), 7.87 (d, 2H), 8.44 (s, 1H).

Example 8 (Comparative)

Preparation of 7-methoxy-3-(4-methyl-benzoyl)coumarin

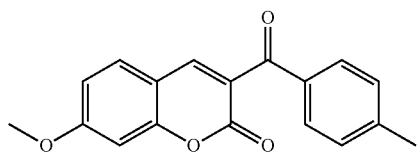

0.4 g (2.60 mmol) of 4-methoxy-2-hydroxy-benzaldehyde were added to a solution of 0.5 g (2.60 mmol) of 3-oxo-3-p-tolyl-propionic acid methyl ester (purchase from Aldrich) and 0.22 g (2.60 mmol) of piperidine in 5 ml of ethanol. After 2 hrs under reflux the reaction mixture was cooled down. The reaction product, crystallized at room temperature, was recovered by filtration. 0.36 g (yield 50%) of product as white solid were obtain.

$^1$H-NMR (CDCl3, δ ppm): 2.42 (s, 3H), 3.92 (s, 3H), 6.9 (m, 2H), 7.28 (d, 2H), 7.47 (d, 1H), 7.78 (d, 2H), 8.05 (s, 1H)

Example 9 (Comparative)

Preparation of 3-(4-methylbenzoyl)benzo[f]coumarin

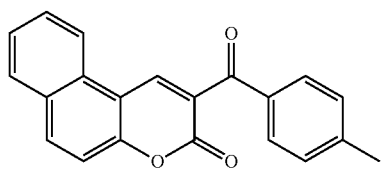 [SMILES: Cc1ccc(C(=O)c2cc3c(ccc4ccccc43)oc2=O)cc1]

0.4 g (2.60 mmol) of 2-hydroxy-naphthalene 1-carbaldehyde, prepared as reported in Example 5, were added to a solution of 0.5 g (2.60 mmol) of 3-oxo-3-p-tolyl-propionic acid methyl ester (purchase from Aldrich) and 0.22 g (2.60 mmol) of piperidine in 5 ml of ethanol. After 2 hrs under reflux the reaction mixture was cooled down. The reaction product, crystallized at room temperature, was recovered by filtration. 0.31 g (yield 40%) of product as yellow solid were obtain.

$^1$H-NMR (CDCl3, δ ppm): 2.44 (s, 3H), 7.30 (d, 2H), 7.52 (d, 1H), 7.60 (t, 1H), 7.71 (t, 1H), 7.82 (d, 2H), 7.94 (d, 1H), 8.10 (d, 1H), 8.25 (d, 1H), 8.88 (s, 1H)

Example 10

Preparation of 3-(4tertbutylbenzoyl)-5,7-dimethoxycoumarin

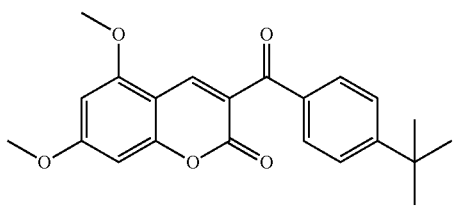 [SMILES: COc1cc(OC)c2cc(C(=O)c3ccc(C(C)(C)C)cc3)c(=O)oc2c1]

0.6 g (3.21 mmol) of 4,6-dimethoxy-2-hydroxy-benzaldehyde, prepared as reported in Example 7, were added to a solution of 0.81 g (3.21 mmol) of methyl 3-(4-t-butylphenyl)-3-oxo-propanoate, prepared as reported in Example 4, and 0.30 g (3.21 mmol) of piperidine in 5 ml of ethanol. After 2 hrs under reflux the reaction mixture was cooled down. The reaction product, crystallized at room temperature, was recovered by filtration. 0.55 g (yield 50%) of product as white solid were obtain.

m.p. 166-168° C.

$^1$H-NMR (CDCl3, δ ppm): 1.34 (s, 9H), 3.90 (s, 6H), 6.3 (d, 1H), 6.45 (d, 1H), 7.47 (d, 2H), 7.80 (d, 2H), 8.40 (s, 1H)

Example 11

Preparation of 7-(sec-butylthio)-3-benzoylcoumarin

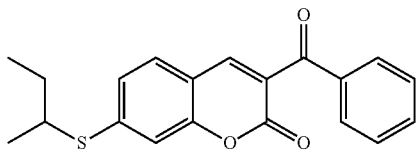 [SMILES: CCC(C)Sc1ccc2cc(C(=O)c3ccccc3)c(=O)oc2c1]

Preparation of 4-(sec-butylthio)-2-hydroxy-benzaldehyde 7.1 g (39 mmoles) of 3-(sec-butylthio)-phenol were added under stirring in nitrogen atmosphere to a solution of 7.89 g (236 mmoles) of anhydrous paraformaldehyde, 14.77 (146 mmoles) of anhydrous triethylamine and 5.6 g (58.5 mmoles) of anhydrous MgCl$_2$ in 150 ml of anhydrous THF. After 2 hrs at 60° C. the reaction mixture was cooled at room temperature, diluted with 100 ml of water and acidified to pH 1 with hydrochloric acid.

The product was extracted with ethylacetate and anhydrified with sodium sulphate.

The solvent was removed by distillation under vacuum obtaining the crude 4-(sec-butylthio)-2-hydroxy-benzaldehyde as a yellow oil.

¹H-NMR (CDCl₃, δ ppm): 1.03 (t, 3H), 1.38 (d, 3H), 1.56-1.82 (m, 2H), 3.36 (q, 1H), 6.80-6.90 (m, 2H), 7.47 (d, 1H), 9.75 (s, 1H).

Preparation of 7-(sec-butylthio)-3-benzoyl coumarin 2.74 g (14.2 mmoles) of ethyl benzoylacetate and 1.2 g (14.2 mmoles) of piperidine were added to a solution of 3 g (14.2 mmoles) of 4-(sec-butylthio)-2-hydroxy-benzaldehyde in 20 ml of ethanol. The mixture was stirred for two hours under reflux, then cooled.

The product was recovered by column chromatography on silica gel (toluene:ethyl acetate 9:1) obtaining 1.92 g (5.68 mmoles, yield 40%) of yellow crystals.

¹H-NMR (CDCl₃, δ ppm): 1.05 (t, 3H), 1.40 (d, 3H), 1.58-1.84 (m, 2H), 3.40 (q, 1H), 7.15-7.26 (m, 2H), 7.40-7.50 (m, 3H), 7.60 (t, 1H), 7.85 (d, 2H), 8.05 (s, 1H)

Evaluation of 3-Ketocoumarine Photoinitiators

Clear Formulations.

The 3-ketocoumarines of the invention were compared with two 3-ketocoumarines of the prior art and two photoinitiators commonly used in the field: Isopropyl Thioxanthone (ITX) and Triphenylphosphine Oxide (TPO).

The photopolymerizable compositions for the test were prepared dissolving the photoinitiators and the co-initiator, Esacure EDB (commercialized by Lamberti S.p.A), at a concentration of 3% by weight (wt) each in a mixture 99.5:0.5 wt of Ebecryl 605 and Ebecryl 350 (Cytec Industries Inc.).

The photopolymerizable compositions, placed in the sample lodgment of a FT-IR (FT-IR 430-Jasco), were exposed to a LED source (400 or 385 nm) located at a distance of 65 mm from the sample and at an angle of 30°. IR spectra were acquired at constant time intervals during the photopolymerization and the reduction over the time of the area of the peaks at 1408 and 810 cm⁻¹ assigned to the acrylic double bond was determined using the IR software.

This allows to quantify the degree of polymerization and therefore the efficiency of the photoinitiator.

The results at 385 and 400 nm, expressed as % of polymerization over the time, are reported in Table 1.

TABLE 1

| Photoinitiator | 385 nm after 1" | 385 nm after 2" | 400 nm after 1" | 400 nm after 2" |
|---|---|---|---|---|
| ITX* | 76 | 77 | 63 | 67 |
| TPO* | 63 | 67 | 48 | 66 |
| Example 1* | <5 | <5 | <5 | <5 |
| Example 2* | <5 | <5 | <5 | <5 |
| Example 3* | 79 | 80 | 64 | 67 |
| Example 4 | 79 | 80 | 63 | 66 |
| Example 5 | 62 | 67 | 48 | 56 |
| Example 6 | 50 | 55 | 46 | 53 |
| Example 7* | n.d. | n.d. | 67 | 69 |

*Comparative
n.d. = not determined

Cyan Inks.

The photopolymerizable compositions for the test were prepared by dissolving the photoinitiators and the co-initiator Esacure EDB at a concentration of 5.0% wt each in a cyan ink for ink-jet printing.

The photopolymerizable composition, placed in the sample lodgment of a FT-IR (FT-IR 430-Jasco), were exposed to a LED source (400 or 385 nm) located at a distance of 65 mm from the sample and at an angle of 30°. IR spectra were acquired at constant time intervals during the photopolymerization and the reduction over the time of the area of the peaks at 1408 cm⁻¹ and 810 cm⁻¹ assigned to the acrylic double bond was determined using the IR software. This allows to quantify the degree of polymerization and therefore the efficiency of the photoinitiator.

The results at 400 or 385 nm, expressed as % of polymerization over the time, are reported in Table 2.

TABLE 2

| Photoinitiator | 385 nm after 1" | 385 nm after 2" | 400 nm after 1" | 400 nm after 2" |
|---|---|---|---|---|
| ITX | 63 | 80 | 32 | 58 |
| TPO* | 8 | 13 | <5 | 10 |
| Example 1* | <5 | <5 | <5 | <5 |
| Example 2* | <5 | <5 | <5 | <5 |
| Example 3* | 21 | 37 | <5 | <5 |
| Example 4 | 44 | 62 | <5 | <5 |
| Example 5 | 54 | 80 | 8 | 21 |
| Example 6 | 65 | 83 | 32 | 57 |
| Example 7* | 24 | 38 | 6 | 12 |
| Example 8* | 33 | 45 | 0 | 0 |
| Example 9* | 8 | 16 | 6 | 11 |
| Example 10 | 75 | 83 | 27 | 45 |
| Example 11 | n.d. | n.d. | 27 | 55 |

*Comparative

The same test were performed with the 400 nm LED source using phenylglycine as co-initiator instead of Esacure EDB at a concentration of 5% wt.

The results, expressed as % of polymerization over the time, are reported in Table 3.

TABLE 3

| Photoinitiator | 400 nm after 1" | 400 nm after 2" |
|---|---|---|
| ITX* | 38 | 72 |
| Example 5 | 31 | 55 |
| Example 6 | 41 | 69 |

*Comparative

The results show that the 3-ketocoumarines of the invention have much better performances as photoinitiators with a LED light source both in clear or pigmented systems than the 3-ketocoumarine of the prior art and have comparable performances with the state of the art photoinitiator.

The invention claimed is:

1. A process for LED photocuring photopolymerizable compositions comprising:
  I) preparing a photopolymerizable composition comprising:
    a) from about 50 to about 99.9% by weight of at least one ethylenically unsaturated compound; and
    b) from about 0.1 to about 35% by weight by weight of at least one 3-ketocoumarine having a general formula I:

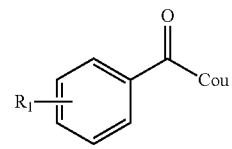

wherein:
R₁ is a substituted or unsubstituted C₂-C₁₂ alkyl group;

Cou is a coumarine group of formula:

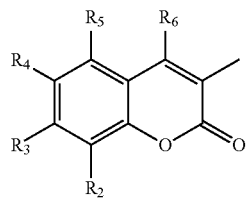

wherein:
at least one of $R_2$ $R_3$, $R_4$ and $R_5$ is —S—$R_7$,
wherein $R_7$ is hydrogen, $C_1$-$C_{12}$ alkyl, $C_3$-$C_{12}$ alkenyl, substituted or unsubstituted phenyl, aryl or heteroaryl, $C_5$-$C_6$ cycloalkyl, $C_1$-$C_{12}$ alkyl which is substituted with SH, —N($C_1$-$C_6$ alkyl)$_2$, piperidino, morpholino, piperazine, —OH, —O($C_1$-$C_{12}$ alkyi), —COOH, and
$R_6$ is hydrogen, a hydroxyl group or an alkyl group having from 1 to 4 carbon atoms; and
II) photopolymerizing the photopolymerizable composition so obtained with a LED light source emitting at wavelengths ranging from 365 nm to 420 nm.

2. The process for photocuring photopolymerizable compositions of claim 1, wherein the photopolymerizable composition comprises:
a) from about 70 to about 98.9% by weight of at least one ethylenically unsaturated compound;
b) from about 0.1 to about 20% by weight of at least one 3-ketocoumarine of formula I.

3. The process for photocuring photopolymerizable compositions according to claim 1, wherein the photopolymerizable composition further comprises from about 0.2 to about 15% by weight of at least one co-initiator and/or from about 0.5 to about 15% by weight of at least one additional photoinitiator.

4. The process for photocuring photopolymerizable compositions of claim 3, wherein the photopolymerizable composition comprises from about 70 to about 98.9% by weight of at least one photopolymerizable compound, from about 0.1 to about 10% by weight of at least one 3-ketocoumarine of formula I, from about 1 to about 15% by weight at least one sensitizable photoinitiator and, optionally, from about 0.2 to about 8% by weight of a co-initiator.

5. The process for photocuring photopolymerizable compositions of claim 1, wherein the photopolymerizable composition further comprises: c) from 0.01 to 30% by weight of colorants.

6. The process for photocuring photopolymerizable compositions of claim 5, wherein the photopolymerizable composition comprises:
a) from about 70 to about 98.9% by weight of at least one ethylenically unsaturated compound;
b) from about 0.1 to about 20% by weight of at least one 3-ketocoumarine of formula I.

7. The process for photocuring photopolymerizable compositions according to claim 5, wherein the photopolymerizable composition further comprises from about 0.2 to about 15% by weight of at least one co-initiator and/or from about 0.5 to about 15% by weight of at least one additional photoinitiator.

8. The process for photocuring photopolymerizable compositions of claim 7, wherein the photopolymerizable composition comprises from about 70 to about 98.9% by weight of at least one photopolymerizable compound, from about 0.1 to about 10% by weight of at least one 3-ketocoumarine of formula I, from about 1 to about 15% by weight at least one sensitizable photoinitiator and, optionally, from about 0.2 to about 8% by weight of a co-initiator.

9. The process for photocuring photopolymerizable compositions of claim 5, wherein the colorants are colorants for ink-jet printing.

10. A composition comprising 3-ketocoumarines having a general formula I:

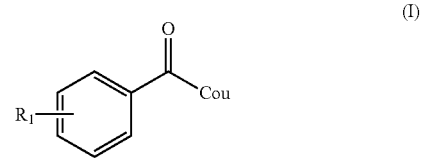

wherein:
$R_1$ is a substituted or unsubstituted $C_2$-$C_{12}$ alkyl group;
Cou is a coumarine group of formula:

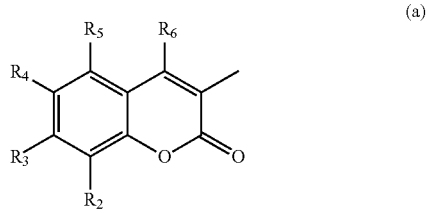

wherein
at least one of $R_2$ $R_3$, $R_4$ and $R_5$ is —S—$R_7$,
wherein $R_7$ is hydrogen, $C_1$-$C_{12}$ alkyl, $C_3$-$C_{12}$ alkenyl, substituted or unsubstituted phenyl, aryl or heteroaryl, $C_5$-$C_6$ cycloalkyl, $C_1$-$C_{12}$ alkyl which is substituted with SH, —N($C_1$-$C_6$ alkyl)$_2$, piperidino, morpholino, piperazine, —OH, —O($C_1$-$C_{12}$ alkyi), —COOH, and
$R_6$ is hydrogen, a hydroxyl group or an alkyl group having from 1 to 4 carbon atoms.

11. The composition of claim 10 wherein $R_7$ is an alkyl group having from 1 to 6 carbon atoms.

12. A composition comprising 3-ketocoumarines having a general formula I:

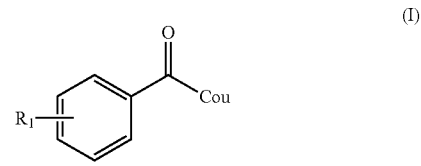

wherein:
$R_1$ is a substituted or unsubstituted $C_2$-$C_{12}$ alkyl group; and Cou is a coumarine group of formula:

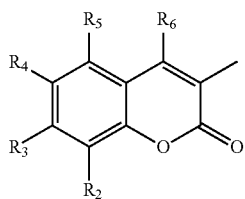
(a)

wherein
at least one of $R_2$ $R_3$, $R_4$ and $R_5$ is an alkoxy group having from 1 to 6 carbon atoms and $R_6$ is hydrogen, a hydroxyl group or an alkyl group having from 1 to 4 carbon atoms;

or Cou is a substituted or unsubstituted naphtho-coumarine having a general formula selected from the group consisting of:

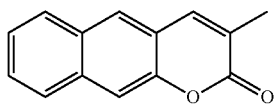
(b)

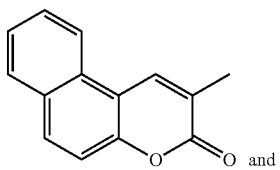
(c)

and

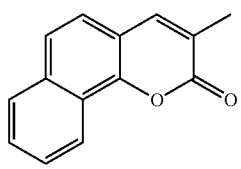
(d)

13. A process for LED photocuring photopolymerizable compositions comprising:

I) preparing a photopolymerizable composition comprising:
a) from about 50 to about 99.9% by weight of at least one ethylenically unsaturated compound; and
b) from about 0.1 to about 35% by weight by weight of at least one 3-ketocoumarine having a general formula I:

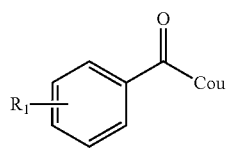
I wherein:
$R_1$ is a substituted or unsubstituted $C_2$-$C_{12}$ alkyl group;

Cou is a coumarine group of formula:

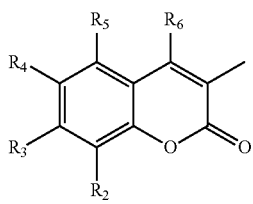
(a)

wherein:
$R_2$, $R_3$, $R_4$ and $R_5$ are, independently of one another, hydrogen; or —S—$R_7$, wherein $R_7$ is hydrogen, $C_1$-$C_{12}$ alkyl, $C_3$-$C_{12}$ alkenyl, substituted or unsubstituted phenyl, aryl or heteroaryl, $C_5$-$C_6$ cycloalkyl, $C_1$-$C_{12}$ alkyl which is substituted with SH, —N($C_1$-$C_6$ alkyl) piperidino, morpholino, piperazino, —OH, —O($C_1$-$C_{12}$ alkyl), —COOH; or $C_1$-$C_{12}$ alkoxy;
$R_6$ is hydrogen, a hydroxyl group, an alkyl group having from 1 to 4 carbon atoms;

or Cou is a substituted or unsubstituted naphtho-coumarine group having a general formula selected from the group consisting of:

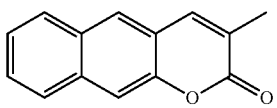
(b)

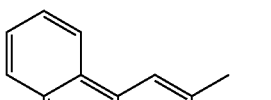
(c)

and

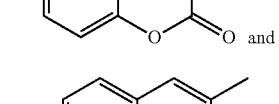
(d)

wherein at least one of $R_2$, $R_3$, $R_4$ and $R_5$ is different from H and that, when Cou is (a) and at least one of $R_2$, $R_3$, $R_4$ and $R_5$ is $C_1$-$C_{12}$ alkoxy or when Cou is (b), (c) or (d), $R_1$ is a substituted or an unsubstituted $C_1$-$C_{12}$ alkyl group; and II) photopolymerizing the photopolymerizable composition so obtained with a LED light source emitting at wavelengths ranging from 365 nm to 420 nm; and
wherein:
in the 3-ketocoumarine of formula I, Cou is a coumarine group of formula (a) and at least one of $R_2$ $R_3$, $R_4$ and $R_5$ is —S—$R_7$ and $R_7$ is an alkyl group having from 1 to 6 carbon atoms;
in the 3-ketocoumarine of formula I, Cou is a coumarine group of formula (a) in which $R_6$ is hydrogen, at least two of $R_2$ $R_3$, $R_4$ and $R_5$ are a $C_1$-$C_6$ alkoxy group and $R_1$ is substituted or unsubstituted $C_1$-$C_{12}$ alkyl group; or in the 3-ketocoumarine of formula I, Cou is an unsubstituted naphtho-coumarine group of formula (b), (c) or (d).

14. The process for photocuring photopolymerizable compositions of claim 13, wherein the photopolymerizable composition further comprises: c) from 0.01 to 30% by weight of colorants.

15. The process for photocuring photopolymerizable compositions of claim 14, wherein the photopolymerizable composition comprises:
   a) from about 70 to about 98.9% by weight of at least one ethylenically unsaturated compound;
   b) from about 0.1 to about 20% by weight of at least one 3-ketocoumarine of formula I.

* * * * *